United States Patent
Zhang et al.

(10) Patent No.: US 10,026,984 B2
(45) Date of Patent: Jul. 17, 2018

(54) MULTI-ELECTRON REDOX ACTIVE MOLECULES FOR ENERGY STORAGE APPLICATIONS

(71) Applicant: UChicago Argonne, LLC, Chicago, IL (US)

(72) Inventors: Lu Zhang, Lisle, IL (US); Jinhua Huang, Willowbrook, IL (US); Zhengcheng Zhang, Naperville, IL (US); Anthony K. Burrell, Naperville, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 156 days.

(21) Appl. No.: 14/840,853

(22) Filed: Aug. 31, 2015

(65) Prior Publication Data

US 2017/0062862 A1    Mar. 2, 2017

(51) Int. Cl.
*H01M 8/18* (2006.01)
*C07C 211/51* (2006.01)
(Continued)

(52) U.S. Cl.
CPC ........... *H01M 8/188* (2013.01); *C07C 211/51* (2013.01); *C07C 211/52* (2013.01);
(Continued)

(58) Field of Classification Search
None
See application file for complete search history.

(56) References Cited

U.S. PATENT DOCUMENTS

| 7,615,312 B2 | 11/2009 | Dahn et al. |
| 7,615,317 B2 | 11/2009 | Dahn et al. |

(Continued)

FOREIGN PATENT DOCUMENTS

WO    WO 2015053588 A1 *  4/2015  ............ H01M 8/188

OTHER PUBLICATIONS

Brushett, F. R. et al., "An All-Organic Non-aqueous Lithium-Ion Redox Flow Battery," Adv. Energy Mater., 2: 1390-1396 (2012).
(Continued)

*Primary Examiner* — Katie L Hammer
(74) *Attorney, Agent, or Firm* — Foley & Lardner LLP

(57) ABSTRACT

A non-aqueous redox flow battery includes a catholyte including a compound of formula (I) or a compound of formula (II):

(Continued)

Where $X^1$ is a moiety of formula I-A or I-B:

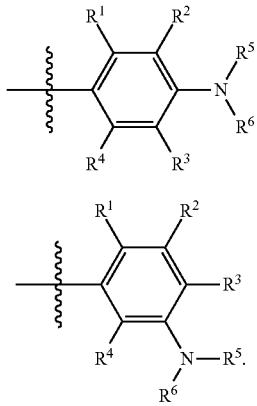

20 Claims, 4 Drawing Sheets

(51) Int. Cl.
C07C 211/52 (2006.01)
C07C 211/54 (2006.01)
H01M 8/02 (2016.01)
H01M 8/20 (2006.01)
C07C 217/08 (2006.01)

(52) U.S. Cl.
CPC .......... C07C 211/54 (2013.01); C07C 217/08 (2013.01); H01M 8/18 (2013.01); *H01M 2300/0025* (2013.01)

(56) References Cited

U.S. PATENT DOCUMENTS

| | | |
|---|---|---|
| 2012/0077068 A1 | 3/2012 | Wang et al. |
| 2012/0077084 A1 | 3/2012 | Christensen et al. |
| 2013/0189571 A1* | 7/2013 | Abouimrane ........... H01M 4/60 429/188 |
| 2013/0224538 A1 | 8/2013 | Jansen et al. |
| 2014/0050999 A1 | 2/2014 | Tolmachev |
| 2015/0255803 A1 | 9/2015 | Delnick et al. |
| 2016/0233536 A1* | 8/2016 | Oh ........................ H01M 8/188 |
| 2017/0187059 A1 | 6/2017 | Potash et al. |

OTHER PUBLICATIONS

Kaur A.P. et al., "A Highly Soluble Organic Catholyte for Non-Aqueous Redox Flow Batteries," Energy Technol. 2000, 00, 1-5.
Wang, W. et al., "Recent Progress in Redox Flow Battery Research and Development," Adv. Funct. Mater., 23: 970-986 (2013).
Notice of Allowance in U.S. Appl. No. 14/840,935, dated Feb. 9, 2018 (9 pages).

* cited by examiner

MULTI-ELECTRON REDOX ACTIVE MOLECULES FOR ENERGY STORAGE APPLICATIONS

GOVERNMENT RIGHTS

The United States Government has rights in this invention pursuant to Contract No. DE-AC02-06CH11357 between the U.S. Department of Energy and UChicago Argonne, LLC, representing Argonne National Laboratory.

FIELD

The present technology relates to redox flow batteries. More particularly, the technology relates to non-aqueous cation-based redox flow batteries utilizing organic redox materials.

BACKGROUND

Energy storage systems are crucial for extensive deployment of renewable energy, such as solar and wind, considering the intermittent nature of these energy sources. Redox flow batteries (RFB) are regarded as one of the most promising technologies not only due to their ability to store large amounts of power and energy, but also to improve the efficiency of grid transmission and distribution. Unlike conventional secondary batteries, the energy of RFBs is stored in two separate tanks, each having an electroactive species, salt(s), and a solvent. The conversion between electrical energy and electrochemical energy occurs as the liquid electrolyte solutions are pumped from the storage tank to the electrodes in a cell stack. Since the energy of redox flow batteries is supplied from externally stored electrolytes, it offers flexibility in terms of energy, power, quick response and safety concerns.

Limited by the water electrolysis potential window (typically 1.2-1.6 V) and the concentration of the active material, traditional aqueous RFBs are hindered by low energy density profiles. As an emerging energy storage system, non-aqueous RFBs have attracted attention due to a wider operational potential window which directly impacts the system energy and power density.

In contrast to their aqueous counterparts, only a few non-aqueous flow batteries have been reported. The majority of the reported non-aqueous flow batteries are anion-exchange systems which employ single electrolytes composed of metal-centered coordination complexes.

SUMMARY

In one aspect, a non-aqueous redox flow battery (RFB) is provided, the RFB including a negative electrode (which functions as a current collector) immersed in a first liquid electrolyte (also referred to herein as a "negative electrolyte" or "anolyte"), a positive electrode (which also functions as a current collector) immersed in a second liquid electrolyte (also referred to herein as a "positive electrolyte" or "catholyte"), and a cation-permeable separator (e.g., a membrane or other cation-permeable material) partitioning the negative electrode/anolyte from the positive electrode/catholyte. During charging and discharging, the electrolytes are circulated over their respective electrodes, while cations shuttle between the two electrolytes to balance the charges that develop as a result of oxidation and reduction of components in the electrolytes.

In some embodiments, the present technology provides a non-aqueous redox flow battery comprising:
a catholyte comprising a compound of formula (I) or a compound of formula (II):

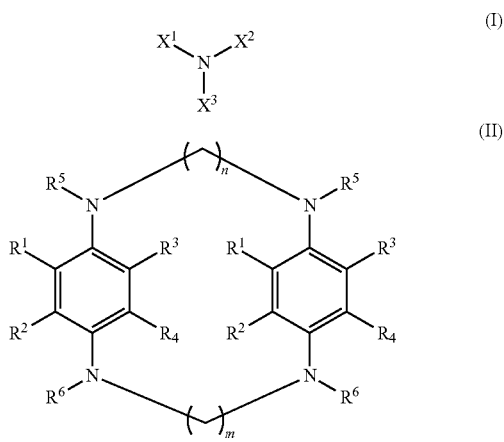

wherein:
$X^1$ is a moiety of formula I-A or I-B:

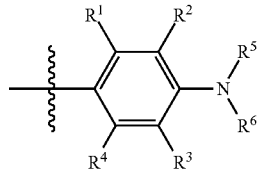

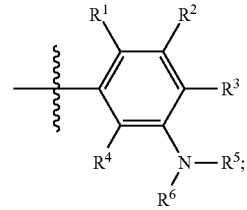

and
$X^2$ and $X^3$ are independently H, alkyl, alkenyl, haloalkyl, heteroalkyl, aryl, or a moiety of formula I-A or I-B;
wherein $R^1$, $R^2$, $R^3$, and $R^4$ are each independently H, —$OR^{10}$, —$NO_2$, F, Cl, Br, I, alkyl, haloalkyl, aryl, heteroalkyl, phosphate, P(=O)($R^{10}$)$_2$, P(=O)(O$R^{10}$)$_2$, —C(O)$R^{11}$, or —S(O)$_2R^{11}$;
each $R^5$ and $R^6$ are independently H, alkyl, alkenyl, haloalkyl, heteroalkyl, or aryl;
each $R^{10}$ is H, alkyl, heteroalkyl, or aryl;
each $R^{11}$ is H, alkyl, heteroalkyl or aryl; and
m and n are independently 1 to 8.

In some embodiments of the compound of formula (I), $X^1$ is a moiety of formula I-A.

In some embodiments of the compound of formula (I), $X^1$ is a moiety of formula I-A, and $X^2$ and $X^3$ are independently H, alkyl, alkenyl, haloalkyl, heteroalkyl, or aryl. In particular embodiments, $X^1$ is a moiety of formula I-A, and $X^2$ and $X^3$ are independently —$C_1$-$C_6$ alkyl, —$C_1$-$C_7$ heteroalkyl, —$C_1$-$C_6$ haloalkyl, or —$C_1$-$C_6$ alkenyl.

In some embodiments of the compound of formula (I), $X^1$ and $X^2$ are independently a moiety of formula I-A and $X^3$ is H, alkyl, alkenyl, haloalkyl, heteroalkyl, or aryl. In particular embodiments of the compound of formula (I), $X^1$ and $X^2$ are independently a moiety of formula I-A and $X^3$ is —$C_1$-$C_6$ alkyl, —$C_1$-$C_7$ heteroalkyl, —$C_1$-$C_6$ haloalkyl, or —$C_1$-$C_6$ alkenyl.

In some embodiments of the non-aqueous redox flow battery of the present technology, the catholyte comprises a compound of formula (I), wherein $X^2$ and $X^3$ are independently —$CH_2CH_2OCH_3$, —$(CH_2CH_2O)_2CH_3$, or —$CH_2CH_2CH=CH_2$.

In some embodiments of the compound of formula (I), $X^1$, $X^2$, and $X^3$ are moieties of formula I-A. In particular embodiments, $X^1$, $X^2$, and $X^3$ are the same.

In some embodiments of the non-aqueous redox flow battery of the present technology, the catholyte comprises a compound of formula (I) or formula (II), $R^1$, $R^2$, $R^3$, and $R^4$ are independently H, F, Cl, Br, I, alkyl, haloalkyl, or heteroalkyl. In particular embodiments of the compound of formula (I) or formula (II), $R^1$, $R^2$, $R^3$, and $R^4$ are independently H, F, —$C_1$-$C_6$ alkyl, or —$C_1$-$C_7$ heteroalkyl.

In some embodiments of the compound of formula (I) or formula (II), $R^5$ and $R^6$ are the same. In particular embodiments, $R^5$ and $R^6$ are independently —$C_1$-$C_6$ alkyl, —$C_1$-$C_7$ heteroalkyl, or —$C_1$-$C_6$ alkenyl. In yet other embodiments, $R^5$ and $R^6$ are —$CH_3$, —$CH_2CH_3$, —$CH_2CH_2OCH_3$, —$(CH_2CH_2O)_2CH_3$, or —$CH_2CH_2CH=CH_2$.

In particular embodiments of the present technology, the compound of formula (I) is

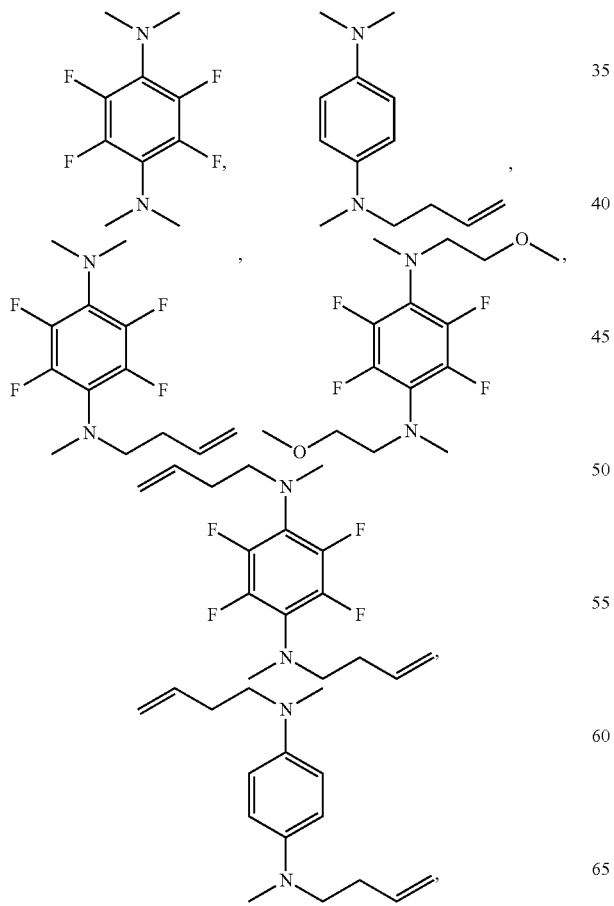

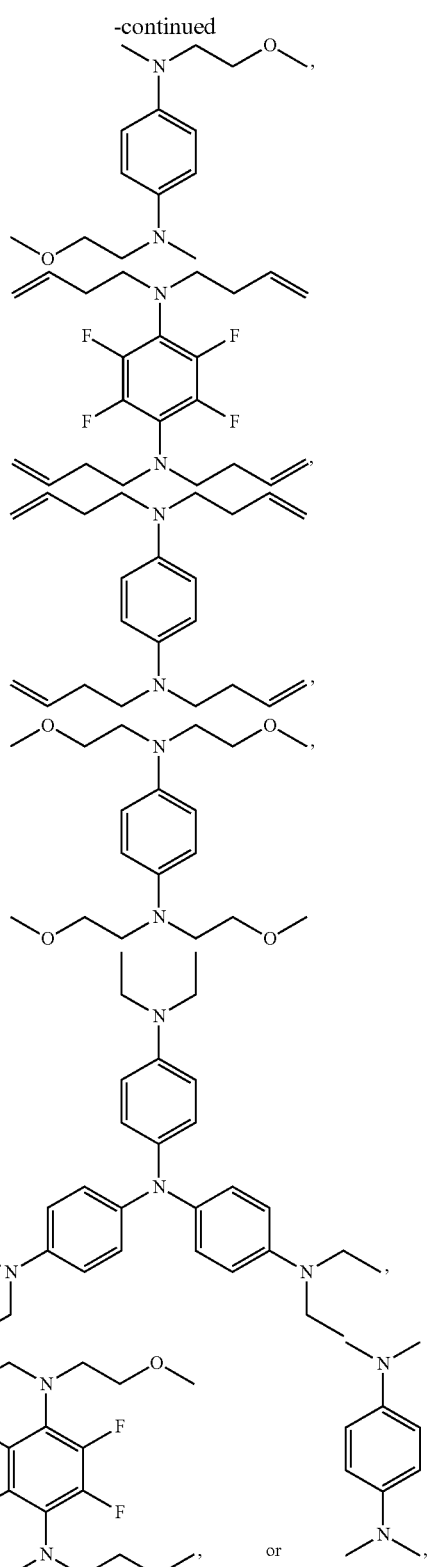

or a combination of any two or more thereof.

In some embodiments of the non-aqueous redox flow battery of the present technology, the catholyte comprises a compound of formula (II).

In particular embodiments, the compound of formula (I) or the compound of formula (II) is N,N,N,N'-tetramethylp-benzenediamine (TMPD), 2,3,5,6-tetrafluoro-$N^1,N^1,N^4,N^4$-tetramethyl-1,4-benzenediamine (TFTMPD), or tris[4-diethylamino-phenyl]amine (TDPA).

In some embodiments, the compound of formula (I) or formula (II) is present in the catholyte from about 0.001 M to about 5.0 M.

In some embodiments, the non-aqueous redox flow battery of the present technology further comprises a solvent and an electrolyte salt. In particular embodiments, the electrolyte salt is present in the catholyte from about 0.1 M to about 2.0 M.

In some embodiments, the electrolyte salt comprises LiBr, LiI, LiSCN, $LiBF_4$, $LiAlF_4$, $LiPF_6$, $LiAsF_6$, $LiClO_4$, $Li_2SO_4$, $LiB(Ph)_4$, $LiAlO_2$, $Li[N(FSO_2)_2]$, $Li[SO_3CH_3]$, $Li[BF_3(C_2F_5)]$, $Li[PF_3(CF_2CF_3)_3]$, $Li[B(C_2O_4)_2]$, $Li[B(C_2O_4)F_2]$, $Li[PF_4(C_2O_4)]$, $Li[PF_2(C_2O_4)_2]$, $Li[CF_3CO_2]$, $Li[C_2F_5CO_2]$, $Li[N(CF_3SO_2)_2]$, $Li[C(SO_2CF_3)_3]$, $Li[N(C_2F_5SO_2)_2]$, $Li[CF_3SO_3]$, $Li_2B_{12}X_{12-n}H_n$, $Li_2B_{10}X_{10-n}H_{n'}$, $Li_2S_{x''}$, $(LiS_{x''}R^{30})_y$, $(LiSe_{x''}R^{30})_y$, or a lithium alkyl fluorophosphate; and further wherein X is a halogen, n is an integer from 0 to 12, n' is an integer from 0 to 10, x'' is an integer from 1 to 20, y is an integer from 1 to 3, and $R^{30}$ is H, alkyl, alkenyl, aryl, ether, F, $-CF_3$, $-COCF_3$, $-SO_2CF_3$, $-SO_2CH_3$, or $-SO_2F$.

In some embodiments, the non-aqueous redox flow battery of the present technology comprises a solvent. In particular embodiments, the solvent is an aprotic solvent. In yet other embodiments, the solvent comprises an organic carbonate, ether, ester, nitrile, or combinations thereof. In specific embodiments, the solvent comprises ethylene carbonate (EC), propylene carbonate (PC), vinylene carbonate (VC), butylene carbonate (BC), dimethyl carbonate (DMC), diethyle carbonate (DEC), ethylmethyle carbonate (EMC), vinyl ethylene carbonate (VEC), dimethyl ether, diglyme, triglyme, or combinations thereof.

In some embodiments of the present technology, the catholyte comprises an additional redox active compound. In particular embodiment, the compound of formula (I) or formula (II) is present at a concentration greater than any additional redox active compound in the solvent.

In some embodiments, the non-aqueous redox flow battery of the present technology further comprises an anode. In particular embodiments, anode comprises Li, Na, or Mg. In some embodiments, the non-aqueous redox flow battery of the present technology further comprises a non-aqueous liquid anolyte. In some embodiments, the anolyte the same or a different solvent than that of the catholyte. In specific embodiments, the anolyte comprises viologen or quinoxaline.

In other embodiments, the non-aqueous redox flow battery of the present technology further comprises a separator positioned between the anolyte and the catholyte.

In some embodiments, the present technology provides a method of operating a redox flow battery, the method comprising:

providing a redox flow battery comprising a compound of formula (I) or a compound of formula (II):

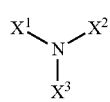

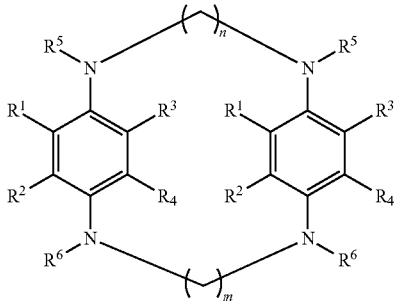

wherein:

$X^1$ is a moiety of formula I-A or I-B:

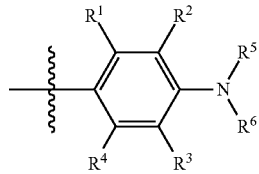

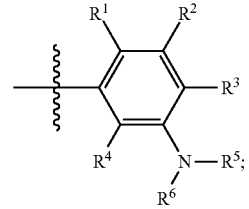

and $X^2$ and $X^3$ are independently H, alkyl, alkenyl, haloalkyl, heteroalkyl, aryl, or a moiety of formula I-A or I-B;

wherein $R^1$, $R^2$, $R^3$, and $R^4$ are each independently H, $-OR^{10}$, $-NO_2$, F, Cl, Br, I, alkyl, haloalkyl, aryl, heteroalkyl, phosphate, $P(=O)(R^{10})_2$, $P(=O)(OR^{10})_2$, $-C(O)R^{11}$, or $-S(O)_2R^{11}$;

each $R^5$ and $R^6$ are independently H, alkyl, alkenyl, haloalkyl, heteroalkyl, or aryl;

each $R^{10}$ is H, alkyl, heteroalkyl, or aryl;

each $R^{11}$ is H, alkyl, heteroalkyl or aryl; and m and n are independently 1 to 8; and operating the redox flow battery at a voltage sufficient to access the second electron redox couple of the compound of Formula (I) or (II).

Figure 3:
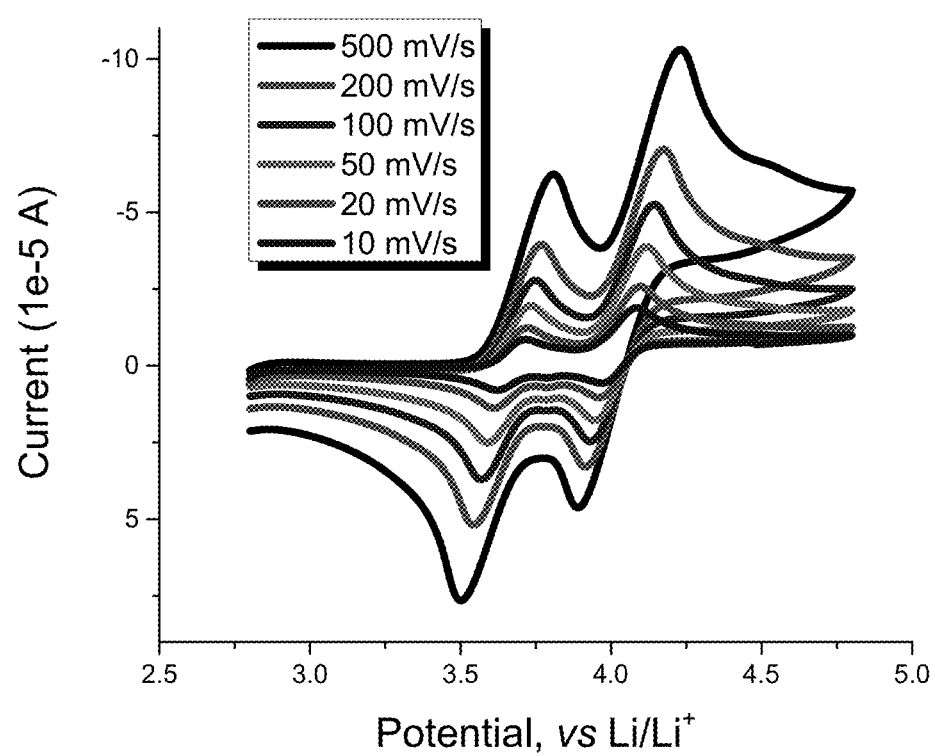

FIG. 3 is a cyclic voltammogram of TFTMPD (10 mM) in 0.5 M LiPF$_6$ in propolene carbonate (PC) at various scan rates using a Pt/Li/Li electrode system, according to the examples.

Figure 4:
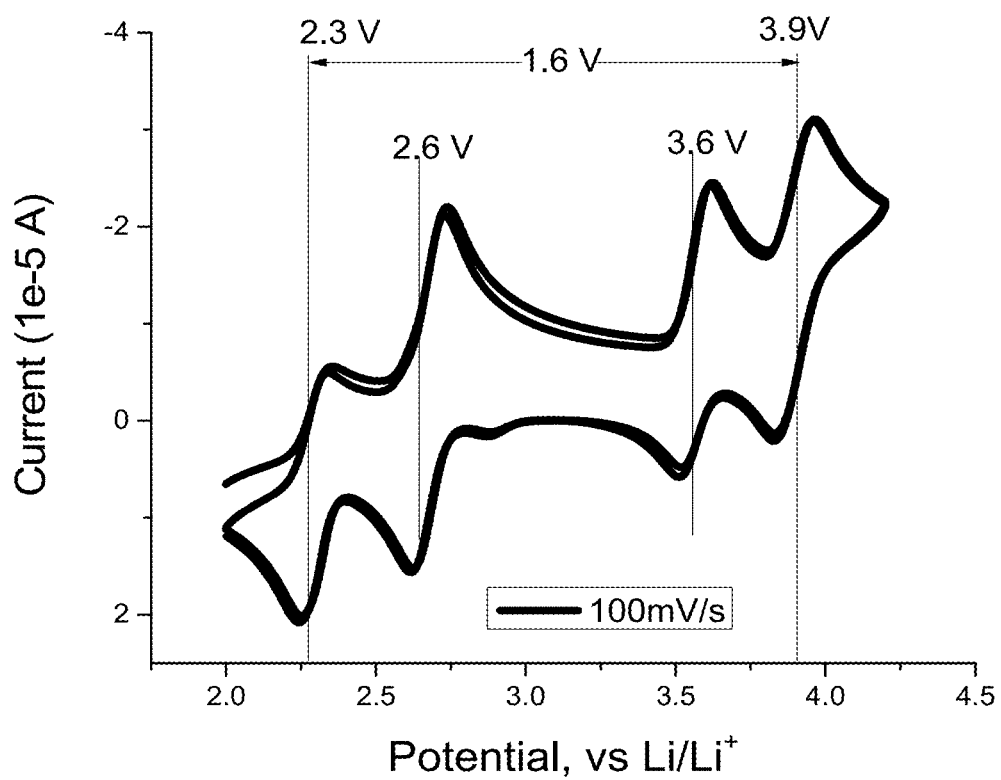

FIG. 4 is a cyclic voltammogram of tris[4-(diethylamino) phenyl]amine (TDPA, 10 mM) in 1.2 M LiPF$_6$ in EC/EMC (3:7 by weight) at a 100 mV/s scan rate using a Pt/Li/Li electrode system, according to the examples.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein may be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In general, "substituted" refers to an alkyl, alkenyl, alkynyl, aryl, or ether group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

As used herein, "alkyl" groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Alkyl groups may be substituted or unsubstituted. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups. As used herein the term haloalkyl is an alkyl group having one or more halo groups. In some embodiments, haloalkyl refers to a per-haloalkyl group.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups may be substituted or unsubstituted. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to: 2,2-; 2,3-; 2,4-; 2,5-; or 2,6-disubstituted cyclohexyl groups or mono-, di-, or tri-substituted norbornyl or cycloheptyl groups, which may be substituted with, for example, alkyl, alkoxy, amino, thio, hydroxy, cyano, and/or halo groups.

Alkenyl groups are straight chain, branched or cyclic alkyl groups having 2 to about 20 carbon atoms, and further including at least one double bond. In some embodiments alkenyl groups have from 1 to 12 carbons, or, typically, from 1 to 8 carbon atoms. Alkenyl groups may be substituted or unsubstituted. Alkenyl groups include, for instance, vinyl, propenyl, 2-butenyl, 3-butenyl, isobutenyl, cyclohexenyl, cyclopentenyl, cyclohexadienyl, butadienyl, pentadienyl, and hexadienyl groups among others. Alkenyl groups may be substituted similarly to alkyl groups. Divalent alkenyl groups, i.e., alkenyl groups with two points of attachment, include, but are not limited to, CH—CH=CH$_2$, C=CH$_2$, or C=CHCH$_3$.

As used herein, "aryl" or "aromatic," groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. The phrase "aryl groups" includes groups containing fused rings, such as fused aromatic-aliphatic ring systems (e.g., indanyl, tetrahydronaphthyl, and the like). Aryl groups may be substituted or unsubstituted.

Heteroalkyl group include straight and branched chain alkyl groups as defined above and further include 1, 2, 3, 4, 5, or 6 heteroatoms independently selected from oxygen, sulfur, and nitrogen. Thus, heteroalkyl groups include 1 to 12 carbon atoms, 1 to 10 carbons or, in some embodiments, from 1 to 8, or 1, 2, 3, 4, 5, or 6 carbon atoms, or any range therein (e.g., 1-4). Examples of heteroalkyl groups include, but are not limited to, —(CH$_2$CH$_2$O)$_{1-5}$CH$_3$, —(CH$_2$)$_{1-6}$O (CH$_2$)$_{1-6}$ CH$_3$, —(CH$_2$)$_{1-6}$NR$_a$(CH$_2$)$_{1-6}$ CH$_3$, —(CH$_2$)$_{1-6}$S (CH$_2$)$_{1-6}$ CH$_3$, —(CH$_2$)$_{1-6}$O(CH$_2$)$_{1-6}$O(CH$_2$)$_{1-6}$ CH$_3$, —(CH$_2$)$_{1-6}$NR$_a$(CH$_2$)$_{1-6}$NR$_a$(CH$_2$)$_{1-6}$CH$_3$, —(CH$_2$)$_{1-6}$O (CH$_2$)$_{1-6}$O(CH$_2$)$_{1-6}$O(CH$_2$)$_{1-6}$CH$_3$, —(CH$_2$)$_{1-6}$NR$_a$ (CH$_2$)$_{1-6}$NR$_a$(CH$_2$)$_{1-6}$NR$_a$(CH$_2$)$_{1-6}$CH$_3$, with the total number of carbon atoms in the heteroalkyl group being 1 to 12 and R$^a$ is a hydrogen or a substituted or unsubstituted alkyl, alkenyl, aryl or aralkyl group. Other examples of heteroalkyl groups include, but are not limited to, groups having different heteroatoms in a single group. Such examples of heteroalkyl groups include, but are not limited to, —(CH$_2$)$_{1-6}$S(CH$_2$)$_{1-6}$O(CH$_2$)$_{1-6}$, —(CH$_2$)$_{1-6}$ NR$_a$(CH$_2$)$_{1-6}$) O(CH2)$_{1-6}$, —(CH$_2$)$_{1-6}$O(CH$_2$)$_{1-6}$ NR$_a$(CH$_2$)$_{1-6}$S(CH$_2$)$_{1-6}$, —(CH$_2$)$_{1-6}$NR$_a$(CH$_2$)$_{1-6}$O(CH$_2$)$_{1-6}$S(CH$_2$)$_{1-6}$, with the total number of carbon atoms in the heteroalkyl group being 1 to 12. In some embodiments, heteroalkyl groups include, but are not limited to, polyoxyethylene groups, such as —(OCH$_2$CH$_2$—)$_{1-5}$CH$_3$, for example, —O(CH$_2$)$_2$ O(CH$_2$)$_2$OCH$_3$, —O(CH$_2$)$_2$O(CH$_2$)$_2$O(CH$_2$)$_2$OCH$_3$, —O(CH$_2$)$_2$O(CH$_2$)$_2$O(CH$_2$)$_2$O(CH$_2$)$_2$OCH$_3$.

Aralkyl groups are substituted aryl groups in which an alkyl group as defined above has a hydrogen or carbon bond of the alkyl group replaced with a bond to an aryl group as defined above. In some embodiments, aralkyl groups contain 7 to 14 carbon atoms, 7 to 10 carbon atoms, e.g., 7, 8, 9, or 10 carbon atoms or any range therein (e.g., 7-8). Aralkyl groups may be substituted or unsubstituted. Substituted aralkyl groups may be substituted at the alkyl, the aryl or both the alkyl and aryl portions of the group. Representative substituted and unsubstituted alkaryl groups include but are not limited to alkylphenyl such as methylphenyl, (chloromethyl)phenyl, chloro(chloromethyl)phenyl, or fused alkaryl groups such as 5-ethylnaphthalenyl.

Heterocyclyl groups are non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass partially unsaturated and saturated ring systems, such as, for example, imidazolinyl and imidazolidinyl groups. The phrase also includes bridged polycyclic ring systems containing a heteroatom such as, but not limited to, quinuclidyl. The phrase also includes heterocyclyl groups that have other groups, such as alkyl, oxo or halo groups, bonded to one of the ring members, referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, pyrrolinyl, piperidyl, piperazinyl, morpholinyl, thiomorpholinyl, tetrahydropyranyl, and tetrahydrothiopyranyl groups. Representative substituted heterocyclyl groups may be mono-substituted or substituted more than once, such as, but not limited to, morpholinyl groups, which are 2-, 3-, 4-, 5-, or 6-substituted, or disubstituted with various substituents such as those listed above. The heteroatom(s) may also be in oxidized form, if chemically possible.

Heteroaryl groups are aromatic ring compounds containing 5 or more ring members, of which one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, imidazolyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. The phrase "heteroaryl groups" includes fused ring compounds and also includes heteroaryl groups that have other groups bonded to one of the ring members, such as alkyl groups, referred to as "substituted heteroaryl groups." Representative substituted heteroaryl groups may be substituted one or more times with various substituents such as those listed above. The heteroatom(s) may also be in oxidized form, if chemically possible.

The term "halogen" or "halo" as used herein refers to bromine, chlorine, fluorine, or iodine. In some embodiments, the halogen is fluorine. In other embodiments, the halogen is chlorine or bromine. The term "halide" as used herein refers to the anion of a halogen, such as bromide, chloride, fluoride, and iodide. In some embodiments, the halide is chloride or iodide.

The terms "alkoxy" refers to a substituted or unsubstituted alkyl group bonded to an oxygen atom. Examples include but are not limited to methoxy and ethoxy. Representative substituted alkoxy groups may be substituted one or more times with substituents such as those listed above, such as methoxymethyl and fluoromethoxy.

There is an ongoing need for new, more efficient, redox flow batteries. The present technology addresses this need by providing a non-aqueous redox flow battery based on oxidation and reduction of organic electroactive materials at the negative and positive electrodes and cation exchange involving transfer of cations such as alkali metal ions (e.g., lithium and sodium), and alkaline earth metal ions (e.g., magnesium and calcium) to balance charges resulting from the redox reactions. In particular, the present technology provides organic redox compounds that are capable of undergoing two or more reversible redox electron transfers. These compounds offer high capacity and high energy density compared to previously known organic redox materials.

The present technology provides redox active compounds for inclusion into a catholyte of a redox flow battery, wherein the redox active compound includes an aromatic system that contains at least one nitrogen atom. Without being bound by theory, it is hypothesized that unlike oxygen atoms, every nitrogen atom conjugated with aromatic system may afford reversible one electron transfer process. Thus, a compound having more than one nitrogen atom according to the present technology would be capable of providing multiple electron transfers for each molecule thus leading to high efficiency of molecular design and an increase in the overall energy density.

In one aspect, the technology is directed to non-aqueous redox flow batteries. In certain embodiments, the redox flow battery includes, consists essentially of, or consists of a negative electrode immersed in an anolyte, a positive electrode immersed in a catholyte, and a cation-permeable separator to allow cations to shuttle between the anolyte and the catholyte during charging and discharging. The negative electrode and positive electrode each act as current collectors.

In some embodiments, the catholyte includes a compound of formula (I):

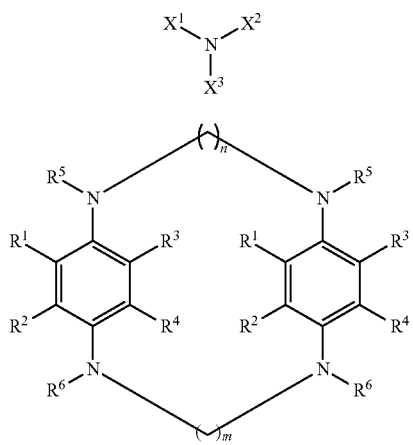

wherein:

$X^1$ is a moiety of formula I-A or I-B:

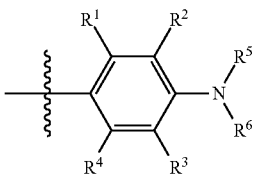

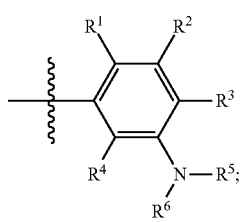

and $X^2$ and $X^3$ are independently H, alkyl, alkenyl, haloalkyl, heteroalkyl, aryl, or a moiety of formula I-A or I-B;

wherein $R^1$, $R^2$, $R^3$, and $R^4$ are each independently H, $-OR^{10}$, $-NO_2$, F, Cl, Br, I, alkyl, haloalkyl, aryl, heteroalkyl, phosphate, $P(=O)(R^{10})_2$, $P(=O)(OR^{10})_2$, $-C(O)R^{11}$, or $-S(O)_2R^{11}$;

each $R^5$ and $R^6$ are independently H, alkyl, alkenyl, haloalkyl, heteroalkyl, or aryl;

each $R^{10}$ is H, alkyl, heteroalkyl, or aryl;

each $R^{11}$ is H, alkyl, heteroalkyl or aryl; and m and n are independently 1 to 8.

In some embodiments, $X^1$ is a moiety of formula I-A. Thus, the compound of formula (I) has the structure I-C:

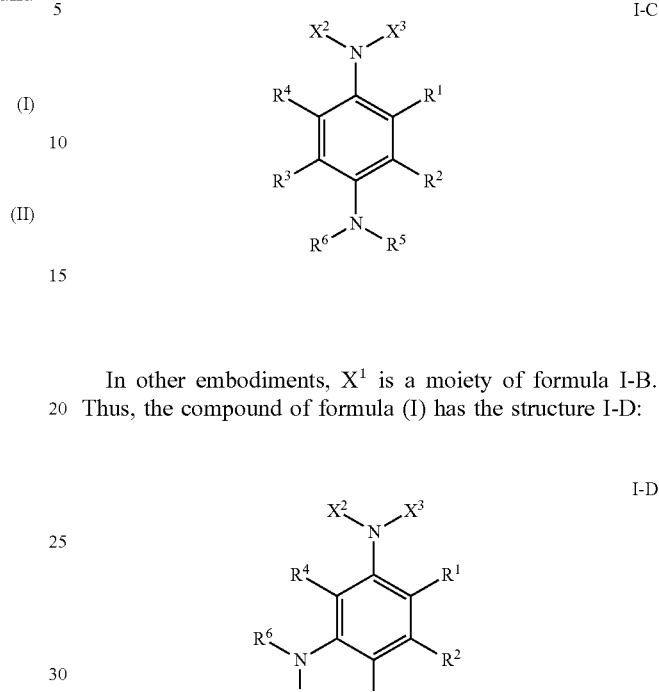

In other embodiments, $X^1$ is a moiety of formula I-B. Thus, the compound of formula (I) has the structure I-D:

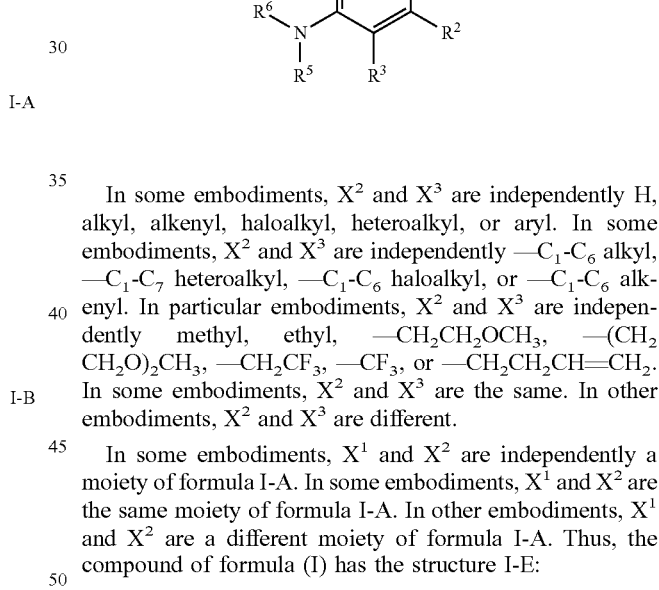

In some embodiments, $X^2$ and $X^3$ are independently H, alkyl, alkenyl, haloalkyl, heteroalkyl, or aryl. In some embodiments, $X^2$ and $X^3$ are independently $-C_1-C_6$ alkyl, $-C_1-C_7$ heteroalkyl, $-C_1-C_6$ haloalkyl, or $-C_1-C_6$ alkenyl. In particular embodiments, $X^2$ and $X^3$ are independently methyl, ethyl, $-CH_2CH_2OCH_3$, $-(CH_2CH_2O)_2CH_3$, $-CH_2CF_3$, $-CF_3$, or $-CH_2CH_2CH=CH_2$. In some embodiments, $X^2$ and $X^3$ are the same. In other embodiments, $X^2$ and $X^3$ are different.

In some embodiments, $X^1$ and $X^2$ are independently a moiety of formula I-A. In some embodiments, $X^1$ and $X^2$ are the same moiety of formula I-A. In other embodiments, $X^1$ and $X^2$ are a different moiety of formula I-A. Thus, the compound of formula (I) has the structure I-E:

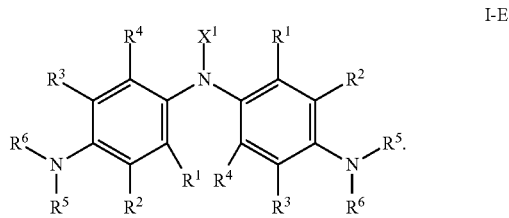

In some embodiments, $X^1$, $X^2$, and $X^3$ are moieties of formula I-A. In some embodiments, $X^1$, $X^2$, and $X^3$ are the same. In other embodiments, $X^1$, $X^2$, and $X^3$ are different. Thus, the compound of formula (I) has the structure I-F:

I-F

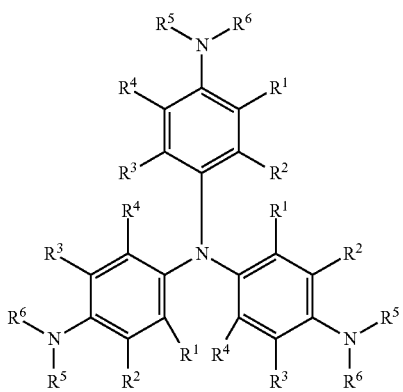

In some embodiments of the present technology, $R^1$, $R^2$, $R^3$, and $R^4$ in any compound of formula (I) are independently H, F, Cl, Br, I, alkyl, haloalkyl, or heteroalkyl. In particular embodiments, $R^1$, $R^2$, $R^3$, and $R^4$ are independently H, F, —$C_1$-$C_6$ alkyl, or —$C_1$-$C_7$ heteroalkyl. In particular embodiments, $R^1$, $R^2$, $R^3$, and $R^4$ are independently H, F, methyl, ethyl, propyl, —$CH_2CH_2OCH_3$, —$(CH_2CH_2O)_2CH_3$, —$CH_2CF_3$, or —$CF_3$. In certain embodiments, $R^1$, $R^2$, $R^3$, and $R^4$ are each H or F. In other embodiments, at least one of $R^1$, $R^2$, $R^3$, and $R^4$ is a group other than H.

In some embodiments of the present technology, $R^5$ and $R^6$ in any compound of formula (I) are independently H, alkyl, alkenyl, haloalkyl, heteroalkyl, or aryl. In some embodiments, at least one of $R^5$ and $R^6$ is a group other than H. In some embodiments, $R^5$ and $R^6$ are independently —$C_1$-$C_6$ alkyl, —$C_1$-$C_7$ heteroalkyl, —$C_1$-$C_6$ haloalkyl, or —$C_1$-$C_6$ alkenyl. In particular embodiments, $R^5$ and $R^6$ are independently methyl, ethyl, —$CH_2CH_2OCH_3$, —$(CH_2CH_2O)_2CH_3$, —$CH_2CF_3$, —$CF_3$, or —$CH_2CH_2CH$=$CH_2$. In some embodiments, $R^5$ and $R^6$ are the same. In other embodiments, $R^5$ and $R^6$ are different.

In some embodiments of the present technology, $R^{10}$ is H, alkyl, heteroalkyl, or aryl. In certain embodiments, $R^{10}$ is H or —$C_1$-$C_6$ alkyl. In specific embodiments, $R^{10}$ is H, methyl, ethyl, or propyl.

In some embodiments of the present technology, $R^{11}$ is H, alkyl, or aryl. In certain embodiments, $R^{11}$ is H or —$C_1$-$C_6$ alkyl. In specific embodiments, $R^{11}$ is H, methyl, ethyl, or propyl.

In specific embodiments, the compound of formula (I) is not $N^1$,$N^1$,$N^4$,$N^4$-tetramethyl-p-phenylenediamine (TMPD).

In specific embodiments, the compound of formula (I) has the structure:

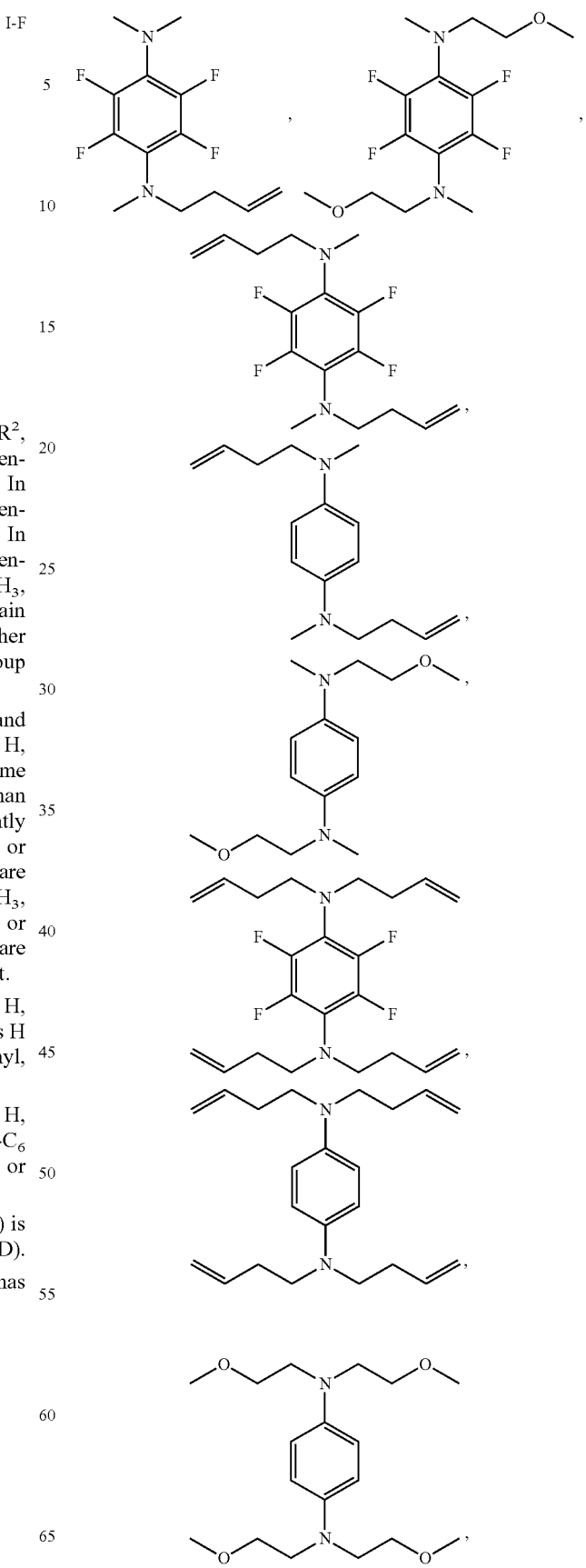

-continued

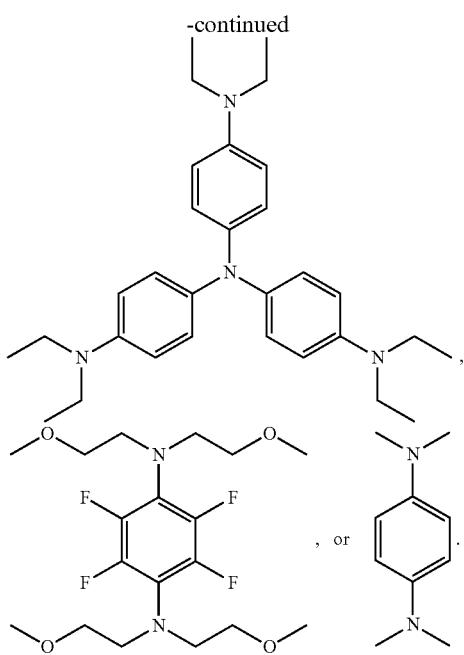

In another aspect, the catholyte includes a compound of formula (II):

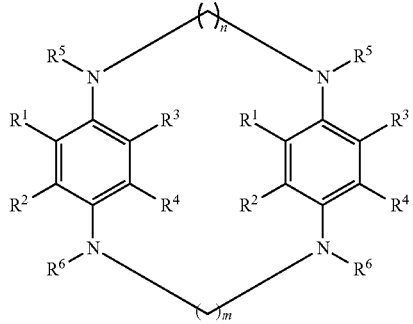

(II)

wherein:
R$^1$, R$^2$, R$^3$, and R$^4$ are each independently H, —OR$^{10}$, —NO$_2$, F, Cl, Br, I, alkyl, haloalkyl, aryl, heteroalkyl, phosphate, P(=O)(R$^{10}$)$_2$, P(=O)(OR$^{10}$)$_2$, —C(O)R$^{11}$, or —S(O)$_2$R$^{11}$;
each R$^5$ and R$^6$ are independently H, alkyl, alkenyl, haloalkyl, heteroalkyl, or aryl;
each R$^{10}$ is H, alkyl, heteroalkyl, or aryl;
each R$^{11}$ is H, alkyl, heteroalkyl or aryl; and
m and n are independently 1 to 8

In some embodiments of the present technology, R$^1$, R$^2$, R$^3$, and R$^4$ in any compound of formula (II) are independently H, F, Cl, Br, I, alkyl, haloalkyl, or heteroalkyl. In particular embodiments, R$^1$, R$^2$, R$^3$, and R$^4$ are independently H, F, —C$_1$-C$_6$ alkyl, or —C$_1$-C$_7$ heteroalkyl. In particular embodiments, R$^1$, R$^2$, R$^3$, and R$^4$ are independently H, F, methyl, ethyl, propyl, —CH$_2$CH$_2$OCH$_3$, —(CH$_2$CH$_2$O)$_2$CH$_3$, —CH$_2$CF$_3$, or —CF$_3$. In certain embodiments, R$^1$, R$^2$, R$^3$, and R$^4$ are each H or F.

In some embodiments of the present technology, R$^5$ and R$^6$ in any compound of formula (II) are independently H, alkyl, alkenyl, haloalkyl, heteroalkyl, or aryl. In some embodiments, R$^5$ and R$^6$ are independently —C$_1$-C$_6$ alkyl, —C$_1$-C$_7$ heteroalkyl, —C$_1$-C$_6$ haloalkyl, or —C$_1$-C$_6$ alkenyl. In particular embodiments, R$^5$ and R$^6$ are independently methyl, ethyl, —CH$_2$CH$_2$OCH$_3$, —(CH$_2$CH$_2$O)$_2$CH$_3$, —CH$_2$CF$_3$, —CF$_3$, or —CH$_2$CH$_2$CH=CH$_2$. In some embodiments, R$^5$ and R$^6$ are the same. In other embodiments, R$^5$ and R$^6$ are different.

In some embodiments of the present technology, the compound of formula (II) has the structure:

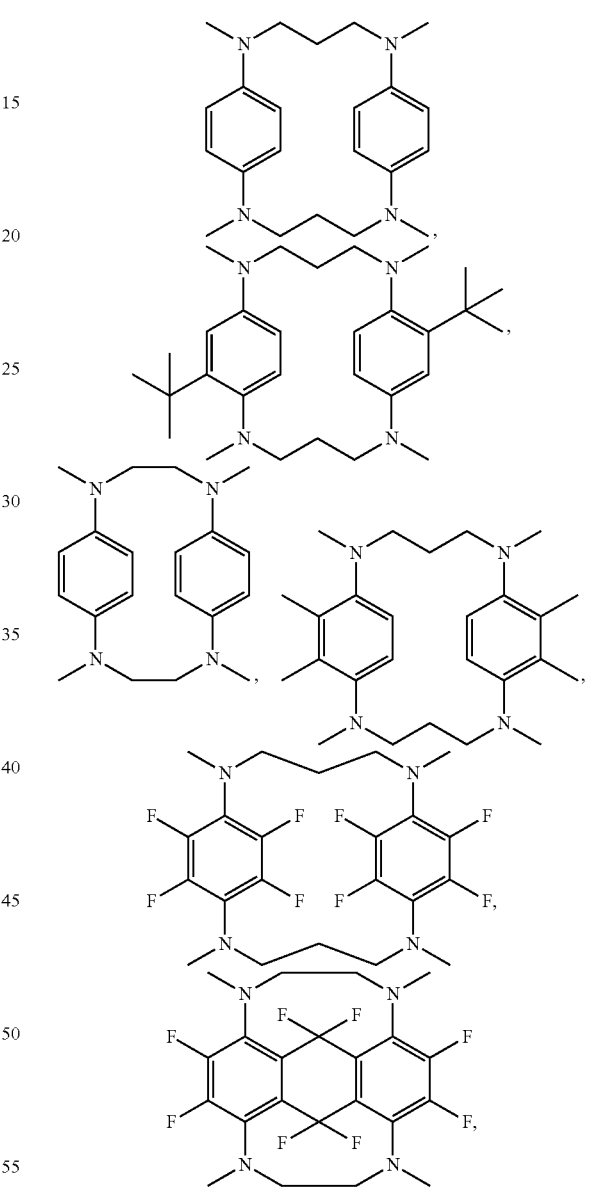

or combinations of two or more thereof.

Without being bound by theory, it is hypothesized that the compound of formula I or compound of formula II undergoes one redox electron transfer process for each amino group in the molecule. Thus, a compound of formula I—C or I-D is capable of undergoing two reversible redox electron transfers. A compound of formula I-E is capable of undergoing three reversible redox electron transfers. Similarly, a compound of formula I-F E is capable of undergoing four reversible redox electron transfers.

In some embodiments, the redox flow battery of the present technology includes a solvent. In certain embodiments, the solvent is an aprotic solvent. In some embodiments, the solvent or solvents of the anolyte may be the same as the solvent or solvents of the catholyte, or the anolyte and catholyte may comprise different solvents. In some embodiments, the solvent includes organic carbonates (e.g., ethylene carbonate, propylene carbonate, ethyl methyl carbonate, and the like), ethers (e.g., diethyl ether, dimethyl ether, tetrahydrofuran, 2-methyl tetrahydrofuran, dimethoxyethane, diglyme, triglyme, and 1,3 dioxolane), esters (e.g., methyl formate, γ-butyrolactone, and methyl acetate), and nitriles (e.g., acetonitrile), or mixture of any two or more thereof. In particular embodiments, the solvent comprises ethylene carbonate (EC), propylene carbonate (PC), vinylene carbonate (VC), butylene carbonate (BC), dimethyl carbonate (DMC), diethyl carbonate (DEC), ethylmethyl carbonate (EMC), vinyl ethylene carbonate (VEC), dimethyl ethyl (DME) or other ethers such as tetrahydrofuran (THF), diglyme (diethylene glycol dimethyl ether), triglyme (triethylene glycol dimethyl ether), or a mixture of any two or more thereof. In specific embodiments, the solvent comprises a mixture of ethyl carbonate and ethylmethyl carbonate at a ratio of about 1:20 to about 20:1 by weight, for example, 1:1, about 2:1, or about 3:7 by weight. In other embodiments, the solvent comprises a mixture of two or more ether solvents, such as dimethyl ether, diglyme, triglyme, and tetrahydrofuran.

In some embodiments, the solvent is a non-aqueous ionic liquid. Examples of the ionic liquid include 1-butyl-3-methylimidazolium tetrafluoroborate ($IMIBF_4$), 1-butyl-3-methylimidazolium hexafluorophosphate (IMIPF6), 1-butyl-4-methylpyridinium tetrafluoroborate (PyBF4), N-methyl-N-propylpiperidinium bis(trifluoromethane sulfonyl) imide (PP13-TFSI), 1-ethyl-3-methlyimidazolium tetrafluoroborate ($EMIBF_4$) or a mixture thereof. In certain embodiments, the solvent is a combination of an aprotic solvent and an non-aqueous ionic liquid.

In some embodiments, the compound of formula (I) or compound of formula (II) is present in the catholyte at a concentration from about 0.001 M to about 5.0 M. In particular embodiments, the compound of formula I or the compound of formula II is present in the catholyte at a concentration of about 0.01 M to about 1.0 M. In some embodiments, the compound of formula (I) or compound of formula (II) is present in the catholyte at a concentration from about 0.005 M to about 1.0 M, from about 0.01 M to about 0.9 M, from about 0.01 M to about 0.8 M, from about 0.01 M to about 0.7 M, from about 0.01 M to about 0.6 M, from about 0.01 M to about 0.5 M, from about 0.01 M to about 0.4 M, from about 0.01 M to about 0.3 M, from about 0.01 M to about 0.2 M, or from about 0.01 M to about 0.1 M. In some embodiments, the compound of formula (I) or compound of formula (II) is present in the catholyte at a concentration of from about 1 mM to about 50 mM, from about 1 mM to about 45 mM, from about 1 mM to about 40 mM, from about 1 mM to about 35 mM, from about 1 mM to about 30 mM, from about 1 mM to about 25 mM, from about 1 mM to about 20 mM, from about 5 mM to about 15 mM. In particular embodiments, the compound of formula (I) or compound of formula (II) is present in the catholyte at a concentration of about 5 mM, about 10 mM, about 15 mM, about 20 mM, about 30 mM, about 40 mM, about 50 mM, about 0.1 M, about 0.2 M, about 0.3 M, about 0.4 M, about 0.5 M, about 0.6 M, about 0.7 M, about 0.8 M, about 0.9 M, about 1.0 M, about 2.0 M, about 3.0 M, about 4.0 M, or about 5.0 M.

Accordingly to some embodiments, the redox flow battery of the present technology includes a negative electrolyte chamber ("NE chamber") that contains the negative electrolyte (i.e., anolyte). The NE chamber is defined by a first housing or enclosure. The NE chamber is adapted to communicate with a first negative electrolyte reservoir ("NE reservoir") and a second NE reservoir (e.g., via openings, valves, tubing, and the like to connect the interior of the housing/enclosure with the interior of the reservoirs). The first NE reservoir, the NE chamber, and the second NE reservoir together define a negative electrolyte circulation pathway. A pump may be positioned within the anolyte circulation pathway to facilitate circulation of the anolyte back and forth between the first NE reservoir and the second NE reservoir over the negative electrode. The pump may be positioned in any convenient location in the anolyte flow pathway (e.g., between the first NE reservoir and the NE chamber, between the second NE reservoir and the NE chamber, or integral with a portion of the NE chamber or NE reservoirs). The negative electrode (i.e., anode) may comprise, consist essentially of, or consist of a metal (e.g., platinum, copper, aluminum, nickel or stainless steel), a carbon material (e.g., carbon black, activated carbon, amorphous carbon, graphite, graphene, or a nanostructured carbon material), lithium, sodium, magnesium, or a combination thereof. The electrode may be porous, fluted, or smooth.

The positive electrode of the battery is positioned within a positive electrolyte chamber ("PE chamber"), which contains the positive electrolyte (i.e., catholyte). The PE chamber is defined by a second housing or enclosure. The PE chamber is adapted to communicate with a first catholyte reservoir ("PE reservoir") and a second PE reservoir (e.g., via openings, valves, tubing, and the like to connect the interior of the housing/enclosure with the interior of the reservoirs). The first PE reservoir, the PE chamber, and the second PE reservoir together define a catholyte circulation pathway. A pump may be positioned within the catholyte circulation pathway to facilitate circulation of the catholyte back and forth between the first PE reservoir and the second PE reservoir over the positive electrode. The pump may be positioned in any convenient location in the catholyte flow pathway (e.g., between the first PE reservoir and the PE chamber, between the second PE reservoir and the PE chamber, or integral with a portion of the PE chamber or PE reservoirs). The positive electrode may comprise, consist essentially of, or consist of a metal (e.g., platinum, copper, aluminum, nickel or stainless steel), a carbon material (e.g., carbon black, activated carbon, amorphous carbon, graphite, graphene, or a nanostructured carbon material), lithium, sodium, magnesium, or a combination thereof. The electrode may be porous, fluted, or smooth.

Pumps suitable for use in the redox flow batteries described herein may include internal gear pumps, screw pumps, shuttle block pumps, flexible vane pumps, sliding vane pumps, circumferential piston pumps, helical twisted root pumps, piston pumps, diaphragm pumps, peristaltic pumps, centrifugal pumps, and the like, which are well known in the liquid pumping art. The utility of a given pump will be dependent on the chemical resistance of the pump to the electrolyte components in contact therewith (i.e., materials compatibility).

In some embodiments, the redox flow battery of the present technology includes a separator situated between the NE chamber and the PE chamber. The separator is adapted to allow cations to flow back and forth between the negative and positive electrolytes upon charging and discharging of the battery. In some embodiments, the separator may be, for example, a cation-permeable membrane, sheet, panel, or film that is permeable to the cations of the electrolytes. In some embodiments, the separator is at least partially impermeable to the redox components of the electrolytes.

In some embodiments, the first and second housings or enclosures for the electrodes are integral with one another, and the cation-permeable separator is mounted as an internal partition separating the NE chamber from the PE chamber. In other embodiments, the first and second housings may be separate components that include perforations or openings that contact the separator, such that cations can flow between the NE chamber and the PE chamber, optionally along with some of the solvent and or redox component, and the separate housings are sealed, e.g. by gaskets, around the partition.

Non-limiting examples of suitable separator materials include, NAFION® type ion exchange membranes (sulfonated tetrafluoroethylene-based fluoropolymer-copolymers), other porous polymeric materials such as, for example, sulfonated poly(ether ether ketones), polysulfones, polyethylene, polypropylene, ethylene-propylene copolymers, polyimides, polyvinyldifluorides, and the like, which may be in the form of membranes, matrix-supported gels, sheets, films, or panels. Other suitable materials include porous ceramics, porous insulated metals, cation-conducting glasses, and zeolites. Alternatively, the separator may be an interface between immiscible liquids. In such case, a porous film, panel, or mesh might be included to aid in maintaining separation between the liquids (e.g., as a physical support or guide to aid in maintaining laminar flow at the interface).

During charging of the battery, an electric potential is applied to the negative and positive electrodes, while simultaneously pumping the negative electrolyte (anolyte) over the negative electrode from the first NE reservoir to the second NE reservoir, and pumping the positive electrolyte (catholyte) over the positive electrode from the first PE reservoir to the second PE reservoir. Cations flow across the cation-permeable separator to balance the charges. The negative redox reactant is reduced and stored in the second NE reservoir, while the positive redox reactant is oxidized and stored in the second PE reservoir. In this way, energy may be stored by charging the battery from an energy source during off-peak usage periods.

During discharge, the electrodes are placed in a circuit (e.g., with a power grid) and the direction of electrolyte flow is reversed, with the stored reduced negative redox reactant being pumped over the negative electrode back into the first NE reservoir, and the stored oxidized positive redox reactant being pumped over the positive electrode back into the first PE reservoir. Cations again flow across the cation-permeable separator (in the opposite direction) to balance the charges. The energy stored in the system may thus be directly used to perform work or can be transferred back into the power grid during peak usage periods to supplement the power supply. An AC/DC converter may be used to facilitate transfer of energy to and from an AC power grid.

In some embodiments, the redox flow battery includes additional redox active compounds. In specific embodiments, the compound of formula (I) or formula (II) is present at a concentration greater than any additional redox active compound in the solvent.

In some embodiments, the redox flow battery of the present technology may include an additional redox active compound in the catholyte or anolyte. In certain embodiments, the redox active compound in the anolyte is a quinoxaline compound (e.g., a quinoxaline compound bearing at least one electron-donating substituent), a dipyridyl ketone compound, a viologen compound (e.g., a bis-benzyl viologen salt, an ethyl viologen salt such as bis-ethyl viologen diperchlorate, and the like), or a benzophenone compound.

In some embodiments, the redox active compound of the positive electrolyte may have a redox potential which is higher than that of the redox potential of the redox active compound in the negative electrolyte.

In some embodiments, the solvent in the redox flow battery of the present technology may further comprise an electrolyte salt. The electrolyte salt components of the anolyte and catholyte may be any electrochemically stable salt. The electrolytes may include a single salt or a combination of two or more salts. The cation component of the salt may be any monovalent (e.g., $Li^+$, $Na^+$, $Ag^+$, $Cu^+$, $NH_4^+$, and the like) or multivalent cation (e.g., $Mg^{2+}$, $Ca^{2+}$, $Cu^{2+}$, $Zn^{2+}$, and the like). In specific embodiments, the cation includes an alkali metal ion, an alkaline earth metal ion, and/or an organic cation. In some embodiments, the electrolyte salts utilized in anolyte and catholyte are alkali metal salts (e.g., lithium salts or sodium salts). In some embodiments, the electrolyte salt is a lithium salt. In specific embodiments, the lithium salt is LiBr, LiI, LiSCN, $LiBF_4$, $LiAlF_4$, $LiPF_6$, $LiAsF_6$, $LiClO_4$, $Li_2SO_4$, $LiB(Ph)_4$, $LiAlO_2$, $Li[N(FSO_2)_2]$, $Li[SO_3CH_3]$, $Li[BF_3(C_2F_5)]$, $Li[PF_3(CF_2CF_3)_3]$, $Li[B(C_2O_4)_2]$, $Li[B(C_2O_4)F_2]$, $Li[PF_4(C_2O_4)]$, $Li[PF_2(C_2O_4)_2]$, $Li[CF_3CO_2]$, $Li[C_2F_5CO_2]$, $Li[N(CF_3SO_2)_2]$, $Li[C(SO_2CF_3)_3]$, $Li[N(C_2F_5SO_2)_2]$, $Li[CF_3SO_3]$, $Li_2B_{12}X_{12-n}H_n$, $Li_2B_{10}X_{10-n'}H_{n'}$, $Li_2S_{x''}$, $(LiS_{x''}R^{30})_y$, $(LiSe_{x''}R^{30})_y$, or a lithium alkyl fluorophosphate; and wherein X is a halogen, n is an integer from 0 to 12, n' is an integer from 0 to 10, x'' is an integer from 1 to 20, y is an integer from 1 to 3, and $R^{30}$ is H, alkyl, alkenyl, aryl, ether, F, $CF_3$, $COCF_3$, $SO_2CF_3$, or $SO_2F$.

In some embodiments, the concentration of the electrolyte salt in the solvent is about 0.01 M to about 10 M, from about 0.05 M to about 5 M, or from about 0.1 M to about 5 M. In specific embodiments, the concentration of the electrolyte salt in the solvent is about 0.1 M, about 0.2 M, about 0.3 M, about 0.4 M, about 0.5 M, about 0.6 M, about 0.7 M, about 0.8 M, about 0.9 M, about 1.0 M, about 1.2 M, about 1.5 M, about 2.0 M, about 3.0 M, about 4.0 M, about 5.0 M, or about 10 M.

EXAMPLES

The following three compounds N,N,N',N'-tetramethyl-p-phenylenediamine (TMPD), 2,3,5,6-tetrafluoro-$N^1$,$N^1$,$N^4$,$N^4$-tetramethyl-1,4-benzenediamine (TFTMPD), and tris[4-(diethylamino)phenyl]amine (TDPA), were tested for their multi-electron redox properties.

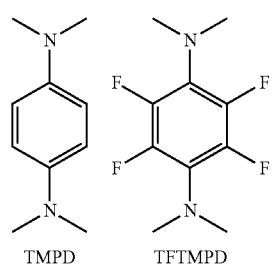

TMPD     TFTMPD

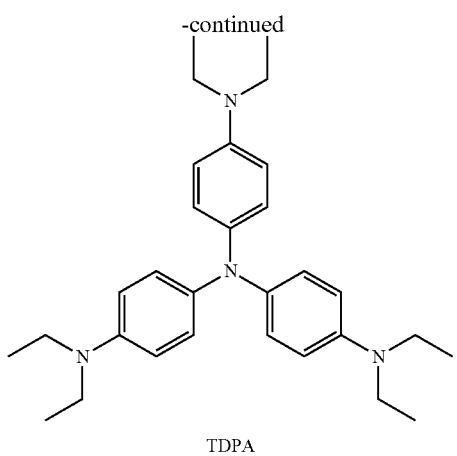

TDPA

Example 1

TFTMPD was prepared according to the following Scheme.

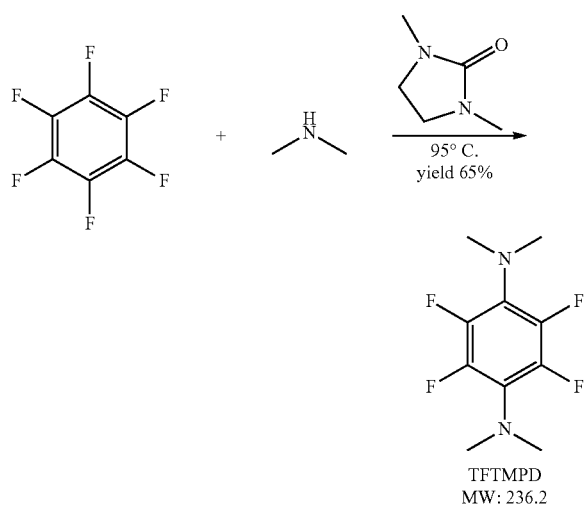

TFTMPD
MW: 236.2

A solution of the perfluorobezene (0.46 mL, 4 mmol), dimethylamine (16 mL, 32 mmol, 2 M in THF), and DMEU (40 mL) in a sealed tube was heated at 95° C. for 24 hours. The reaction mixture was then poured into water (100 mL) and the product was extracted with hexanes (4×50 mL). The organic layer was washed with water (4×50 mL), and dried over $Na_2SO_4$. After the removal of the solvent, the product was purified using silica gel chromatograph (EtOAc:DCM 1:10) to afford pure colorless needle solid (620 mg, yield 65%). The spectral characterizations of TFTPMD are as follows. $^1$H NMR (500 MHz, $CDCl_3$): δ/ppm 2.90 (s, 12H). $^{13}$C NMR (125 MHz, $CDCl_3$): δ/ppm 143.8 (1J, 2J and 3J coupling with adjacent F atoms), 125.8, 43.7. $^{19}$F NMR (470 MHz, $CDCl_3$): δ/ppm 151.68. Mass spectroscopy ($EI^+$): calculated. $M^+$ 236.1. found $M^+$ 236.1.

Example 2

Figure 1:
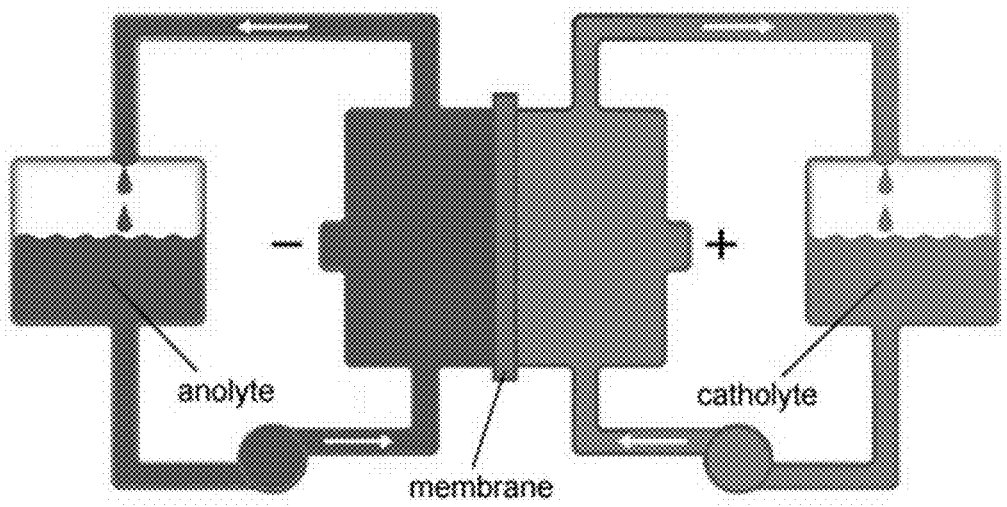
FIG. 1 shows a simplified scheme of a redox flow cell. Two reservoirs containing electrolyte solutions of redox active molecules serve as positive and negative electrodes, referred to as catholyte (high potential material) and anolyte (low potential material), respectively. The intrinsic reversible redox reactions (anodic for catholyte, and cathodic for anolyte) of the redox active molecule are utilized to store the energy during the charging process. Upon discharging, the reversed reaction of the catholyte and anolyte occurs to deliver energy.
Figure 2:
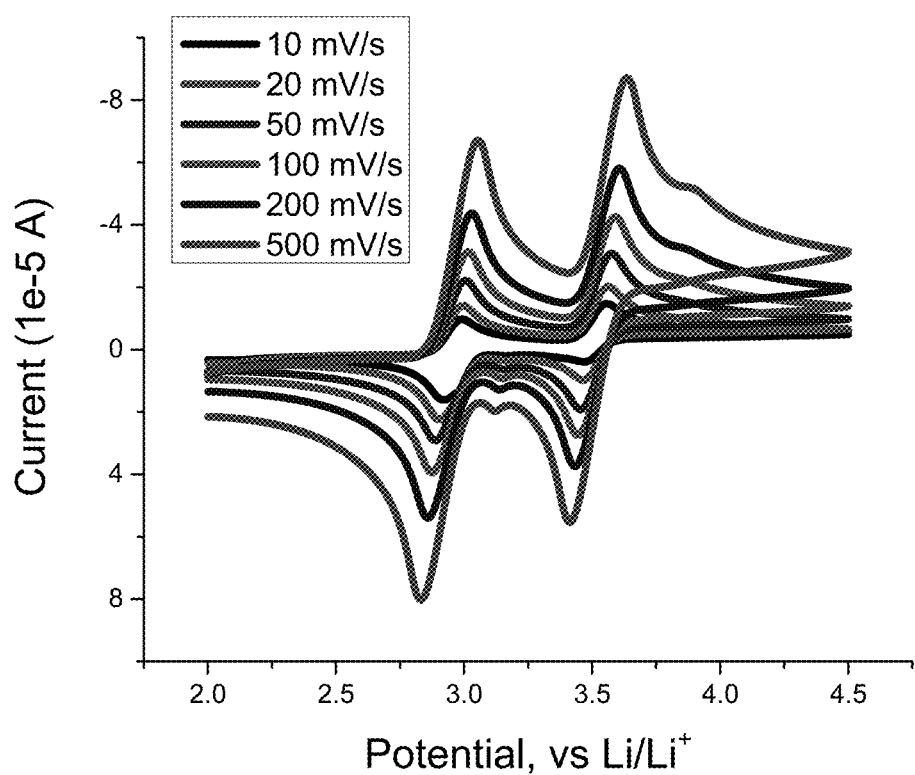
FIG. 2 is a cyclic voltammogram of $N^1,N^1,N^4,N^4$-tetramethyl-p-phenylenediamine (TMPC, 10 mM) in 1.2 M $LiPF_6$ in ethylene carbonate/ethylmethyl carbonate (EC/EMC; 3:7 by weight) at various scan rates using a Pt/Li/Li electrode system, according to the examples.

Redox activity of $N^1,N^1,N^4,N^4$-tetramethyl-p-phenylenediamine (TMPD) is illustrated by the cyclic voltammogram shown in FIG. 2, taken at a 10 mM concentration of TMPC, 1.2 M $LiPF_6$ in ethylene carbonate/ethylmethyl carbonate (EC/EMC; 3:7 by weight) at various scan rates using a Pt/Li/Li electrode system.

As shown in the above structures, TMPD has exhibits reversible two electron transfer process. The first redox couple is around 3.5 V vs Li/Lt and the second one is around 3.9 V. In considering the molecular weight of this compound, the specific molecular weight per electron is only 82.1 g/mol and its intrinsic capacity is as high as 326.3 mAh/g. Combined with the potentials, the energy density against Li is 1044.2 W-h/kg.

Example 3

Redox activity of TFTMPD (10 mM) in 0.5 M $LiPF_6$ in propylene carbonate (PC) at various scan rates using a Pt/Li/Li electrode system is illustrated by the cyclic voltammogram shown in FIG. 3.

Both TMPD and TFTMPD have two amine groups directly linked to benzene ring. Thus, TMPC and TFTMPD may each afford two redox electron transfers. In comparison to TMPD, TFTMPD has similar redox behavior but higher redox potentials due to the incorporated fluorine atoms. The capacity and energy density are relatively lower compared to TMPD (see FIG. 3 and Table 1).

Example 4

Redox activity of TDPA (10 mM) in 1.2 M $LiPF_6$ in EC/EMC (3:7 by weight) at a 100 mV/s scan rate using a Pt/Li/Li electrode system is illustrated by the cyclic voltammogram shown in FIG. 4.

TDPA has 4 amino groups and may therefore exhibit four redox reactions. As seen in FIG. 4, TDPA provides a 4 electron transfer process during the cyclic voltammogram test (see FIG. 4). In view of the molecular weight of TDPA, the specific molecular weight per electron is calculated to be 114.67 and intrinsic capacity is 233.7 mAh/g. Energy density is calculated to be 747.8 W-h/kg.

Table 1 summarizes the properties for TMPD, TFTMPD, and TDPA.

| Compound | Potentials (V, vs $Li/Li^+$) | Molecular Weight per electron (g/mol) | Intrinsic capacity (mAh/g) | Energy Density (W-h/kg) |
| --- | --- | --- | --- | --- |
| TMPD | 2.9, 3.5 | 82.1 | 326.3 | 1044.2 |
| TFTMPD | 3.65, 4.05 | 118.1 | 226.9 | 873.5 |
| TDPA | 2.3, 2.7, 3.6, 3.9 | 114.67 | 233.7 | 747.8 |

All these molecules offer high capacity and high energy density compared to other commercial energy storage techniques. These materials not only could be utilized in no-aqueous flow battery, but also may find applications in other energy storage technologies if properly designed or incorporated in the right form of frameworks.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A non-aqueous redox flow battery comprising:
a catholyte comprising a compound of formula (I) or a compound of formula (II):

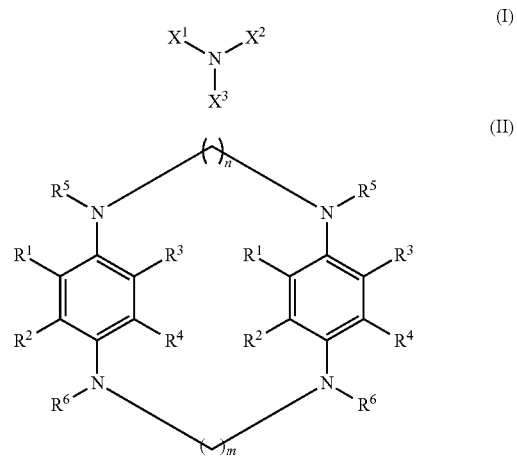

wherein:
X$^1$ is a moiety of formula I-A or I-B:

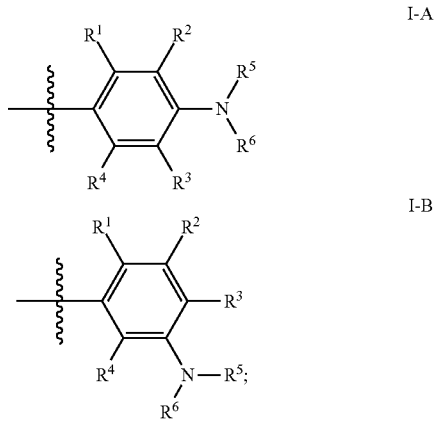

and
X$^2$ and X$^3$ are independently —CH$_2$CH$_2$OCH$_3$, —(CH$_2$CH$_2$O)$_2$CH$_3$ or —CH$_2$CH$_2$CH═CH$_2$; or wherein X$^1$, X$^2$, and X$^3$ are each moieties of formula I-A;
R$^1$, R$^2$, R$^3$, and R$^4$ are each independently H, —OR$^{10}$, —NO$_2$, F, Cl, Br, I, alkyl, haloalkyl, aryl, heteroalkyl, phosphate, P(═O)(R$^{10}$)$_2$, P(═O)(OR$^{10}$)$_2$, —C(O)R$^{11}$, or —S(O)$_2$R$^{11}$;
each R$^5$ and R$^6$ are independently H, alkyl, alkenyl, haloalkyl, heteroalkyl, or aryl;
each R$^{10}$ is H, alkyl, heteroalkyl, or aryl;
each R$^{11}$ is H, alkyl, heteroalkyl or aryl; and
m and n are independently 1 to 8.

2. The non-aqueous redox flow battery of claim 1, wherein X$^1$ is a moiety of formula I-A.

3. The non-aqueous redox flow battery of claim 1, wherein R$^1$, R$^2$, R$^3$, and R$^4$ are independently H, F, Cl, Br, I, alkyl, haloalkyl, or heteroalkyl.

4. The non-aqueous redox flow battery of claim 1, wherein R$^1$, R$^2$, R$^3$, and R$^4$ are independently H, F, —C$_1$-C$_6$ alkyl, or —C$_1$-C$_7$ heteroalkyl.

5. The non-aqueous redox flow battery of claim 1, wherein $R^5$ and $R^6$ are independently —$C_1$-$C_6$ alkyl, —$C_1$-$C_7$ heteroalkyl, or —$C_1$-$C_6$ alkenyl.

6. The non-aqueous redox flow battery of claim 1, wherein $R^5$ and $R^6$ are $CH_3$, —$CH_2CH_3$, —$CH_2CH_2OCH_3$, —$(CH_2CH_2O)_2CH_3$, or —$CH_2CH_2CH$=$CH_2$.

7. A redox flow battery comprising a compound represented by:

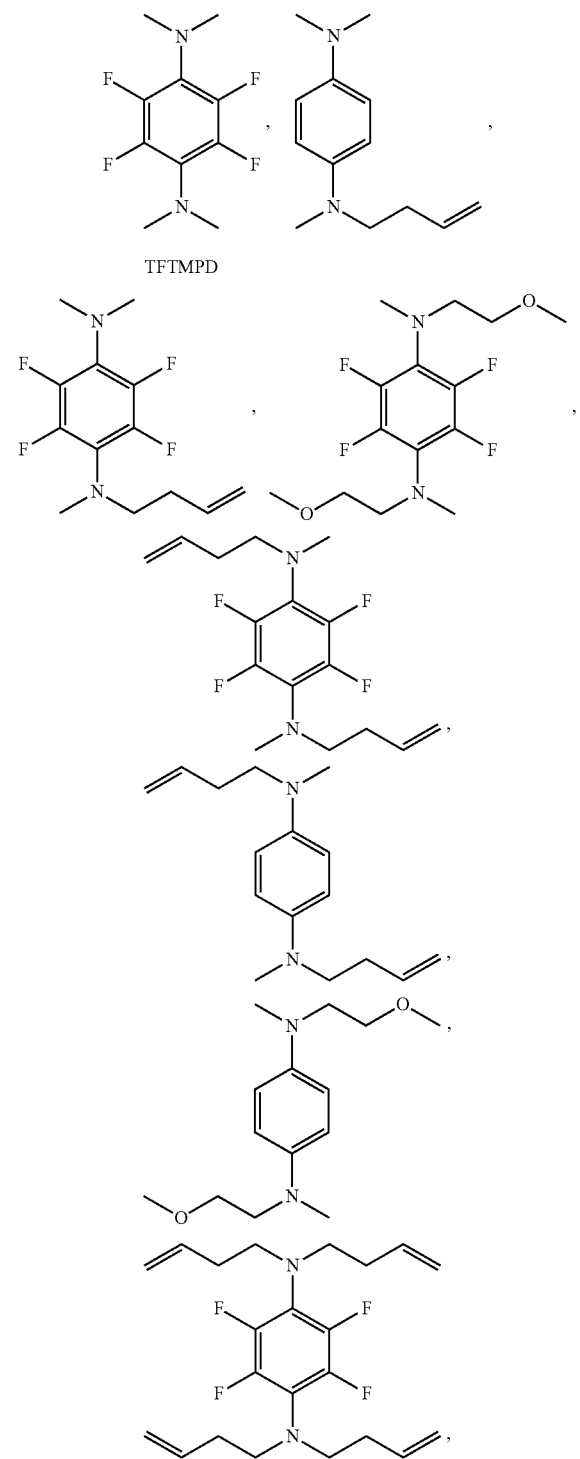

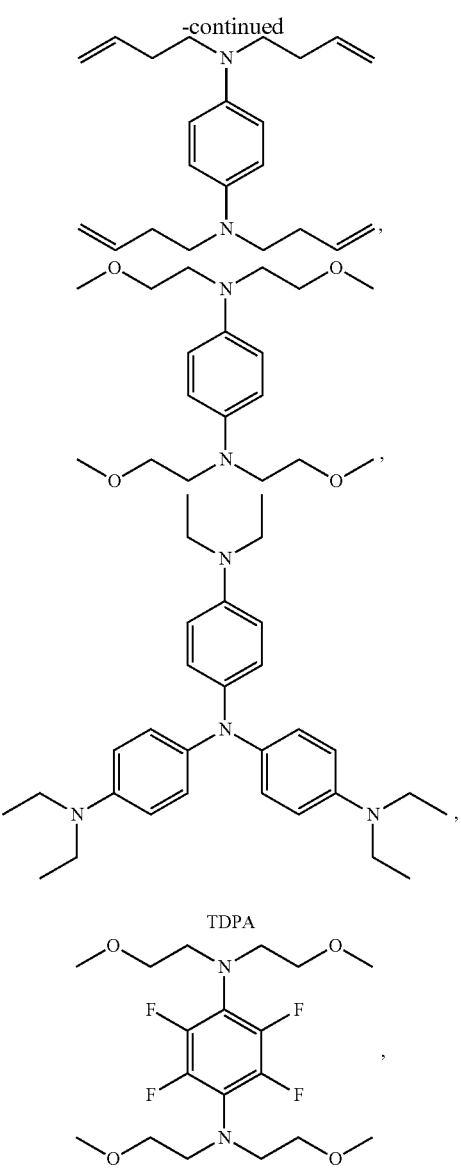

or a combination of any two or more thereof.

8. The non-aqueous redox flow battery of claim 1, wherein the catholyte comprises a compound of formula (II).

9. The non-aqueous redox flow battery of claim 7, wherein the compound is TFTMPD or TDPA.

10. The non-aqueous redox flow battery of claim 1, further comprising a solvent and an electrolyte salt.

11. The non-aqueous redox flow battery of claim 10, wherein the electrolyte salt is present in the catholyte from about 0.1 M to about 2.0 M.

12. The non-aqueous redox flow battery of claim 10, wherein the solvent comprises an organic carbonate, ether, ester, nitrile, or mixture of any two or more thereof.

13. The non-aqueous redox flow battery of claim 1, wherein the catholyte further comprises a solvent and the compound of formula (I) or formula (II) is present at a concentration greater than any additional redox active compound in the solvent.

14. The non-aqueous redox flow battery of claim 1 further comprising an anode, wherein the anode comprises Li, Na, or Mg.

15. The non-aqueous redox flow battery of claim 1 further comprising an anolyte, wherein the anolyte comprises a viologen or a quinoxaline.

16. A method of operating a redox flow battery, the method comprising:

providing a redox flow battery comprising a compound of formula (I) or a compound of formula (II):

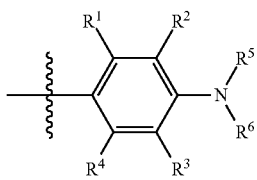
(I)

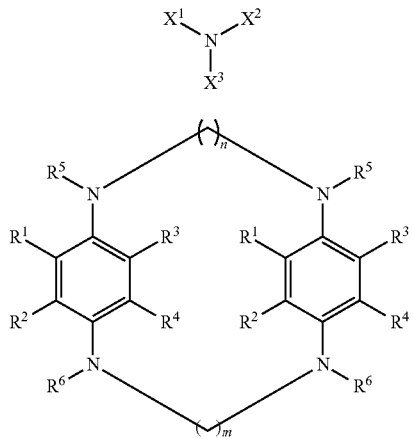
(II)

wherein:

$X^1$ is a moiety of formula I-A or I-B:

(I-A)

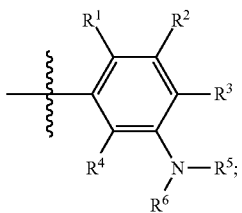

(I-B)

and $X^2$ and $X^3$ are independently —CH$_2$CH$_2$OCH$_3$, —(CH$_2$CH$_2$O)$_2$CH$_3$ or —CH$_2$CH$_2$CH=CH$_2$; or wherein $X^1$, $X^2$, and $X^3$ are each moieties of formula I-A;

$R^1$, $R^2$, $R^3$, and $R^4$ are each independently H, —OR$^{10}$, —NO$_2$, F, Cl, Br, I, alkyl, haloalkyl, aryl, heteroalkyl, phosphate, P(=O)(R$^{10}$)$_2$, P(=O)(OR$^{10}$)$_2$, —C(O)R$^{11}$, or —S(O)$_2$R$^{11}$;

each $R^5$ and $R^6$ are independently H, alkyl, alkenyl, haloalkyl, heteroalkyl, or aryl;

each $R^{10}$ is H, alkyl, heteroalkyl, or aryl;

each $R^{11}$ is H, alkyl, heteroalkyl or aryl; and m and n are independently 1 to 8; and operating the redox flow battery at a voltage sufficient to access a second electron redox couple of the compound of Formula (I) or (II).

17. The redox flow battery of claim 7, further comprising a solvent and an electrolyte salt.

18. The redox flow battery of claim 17, wherein the electrolyte salt is present in the catholyte from about 0.1 M to about 2.0 M.

19. The redox flow battery of claim 17, wherein the solvent comprises an organic carbonate, ether, ester, nitrile, or mixture of any two or more thereof.

20. The redox flow battery of claim 7 further comprising an anode and an anolyte, wherein the anode comprises Li, Na, or Mg, and the anolyte comprises a viologen or a quinoxaline.

* * * * *